(12) United States Patent
Iobbi

(10) Patent No.: US 9,675,455 B2
(45) Date of Patent: Jun. 13, 2017

(54) METHOD OF POSITIONING A MINIMALLY-INVASIVE HEART VALVE WITH CUSP POSITIONERS

(71) Applicant: Edwards Lifesciences Corporation, Irvine, CA (US)

(72) Inventor: Mario Iobbi, Westlake Village, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 15/061,895

(22) Filed: Mar. 4, 2016

(65) Prior Publication Data

US 2016/0184094 A1 Jun. 30, 2016

Related U.S. Application Data

(60) Continuation of application No. 13/653,201, filed on Oct. 16, 2012, now Pat. No. 9,504,567, which is a
(Continued)

(51) Int. Cl.
*A61F 2/24* (2006.01)
*A61B 17/221* (2006.01)
*A61F 2/95* (2013.01)

(52) U.S. Cl.
CPC ............ *A61F 2/243* (2013.01); *A61F 2/2412* (2013.01); *A61F 2/2418* (2013.01);
(Continued)

(58) Field of Classification Search
CPC ....... A61F 2/95–2002/9534; A61F 2210/0023; A61F 2250/0058–2250/0059;
(Continued)

(56) References Cited

U.S. PATENT DOCUMENTS 3,409,013 A 11/1968 Berry
3,548,417 A 12/1970 Kisher
(Continued)

FOREIGN PATENT DOCUMENTS

DE 2246526 A1 3/1973
DE 19532846 A1 3/1997
(Continued)

OTHER PUBLICATIONS

Andersen, et al., Transluminal implantation of artificial heart valves. Description of a new expandable aortic valve and initial results with implantation by catheter technique in closed chest pigs. European Heart Journal, Jan. 1992, 13, pp. 704-708.
(Continued)

*Primary Examiner* — Paul Prebilic
(74) *Attorney, Agent, or Firm* — Klarquist Sparkman LLP

(57) ABSTRACT

A prosthetic heart valve having an internal support frame with a continuous, undulating leaflet frame defined therein. The leaflet frame has three cusp regions positioned at an inflow end intermediate three commissure regions positioned at an outflow end thereof. The leaflet frame may be cloth covered and flexible leaflets attached thereto form occluding surfaces of the valve. The support frame further includes three cusp positioners rigidly fixed with respect to the leaflet frame and located at the outflow end of the support frame intermediate each pair of adjacent commissure regions. The valve is desirably compressible so as to be delivered in a minimally invasive manner through a catheter to the site of implantation. Upon expulsion from catheter, the valve expands into contact with the surrounding native valve annulus and is anchored in place without the use of sutures.

28 Claims, 9 Drawing Sheets

Related U.S. Application Data continuation of application No. 12/170,341, filed on Jul. 9, 2008, now Pat. No. 8,778,018, which is a division of application No. 10/390,951, filed on Mar. 18, 2003, now Pat. No. 7,399,315.

(52) U.S. Cl.
CPC .......... *A61F 2/2427* (2013.01); *A61F 2/2436* (2013.01); *A61B 17/221* (2013.01); *A61F 2002/9522* (2013.01); *A61F 2220/0016* (2013.01); *A61F 2220/0066* (2013.01); *A61F 2220/0075* (2013.01)

(58) Field of Classification Search
CPC ...... A61F 2250/2265; A61F 2250/0004; A61F 2250/0008; A61F 2250/001; A61B 2017/00243; A61B 2017/00238; A61B 2017/00358; A61B 2017/00778; A61B 2017/00783
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,810,474 A | 5/1974 | Cross |
| 4,035,849 A | 7/1977 | Angell et al. |
| 4,056,854 A * | 11/1977 | Boretos .................. A61F 2/2412 128/899 |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goeme et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A * | 11/1998 | Andersen .............. A61F 2/2418 606/108 |
| 5,855,597 A | 1/1999 | Jayaraman |
| 5,855,601 A * | 1/1999 | Bessler ............ A61B 17/32072 623/2.38 |
| 5,855,602 A | 1/1999 | Angell |
| 5,861,028 A | 1/1999 | Angell |
| 5,925,063 A | 7/1999 | Khosravi |
| 5,935,163 A | 8/1999 | Gabbay |
| 5,957,949 A * | 9/1999 | Leonhardt ................ A61F 2/07 606/108 |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 * | 6/2001 | Jayaraman ................ A61F 2/07 623/1.15 |
| 6,299,637 B1 | 10/2001 | Shaolian |
| 6,302,906 B1 | 10/2001 | Goecoechea et al. |
| 6,350,277 B1 | 2/2002 | Kocur |
| 6,425,916 B1 | 7/2002 | Garrison et al. |
| 6,440,164 B1 | 8/2002 | Di Matteo et al. |
| 6,451,052 B1 * | 9/2002 | Burmeister ............. A61F 2/844 623/1.16 |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,605,112 B1 | 8/2003 | Moll |
| 6,730,118 B2 | 5/2004 | Spenser et al. |
| 6,733,525 B2 | 5/2004 | Yang et al. |
| 6,740,111 B1 | 5/2004 | Lauterjung |
| 6,830,584 B1 | 12/2004 | Seguin |
| 6,830,585 B1 * | 12/2004 | Artof .................... A61F 2/2418 623/2.11 |

(56) References Cited

U.S. PATENT DOCUMENTS

| | | | |
|---|---|---|---|
| 6,893,460 B2 | 5/2005 | Spenser et al. | |
| 6,908,481 B2 | 6/2005 | Cribier | |
| 7,018,406 B2 | 3/2006 | Seguin et al. | |
| 7,276,078 B2 | 10/2007 | Spenser et al. | |
| 7,276,084 B2 | 10/2007 | Yang et al. | |
| 7,338,520 B2 | 3/2008 | Bailey et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,618,446 B2 | 11/2009 | Andersen et al. | |
| 7,618,447 B2 | 11/2009 | Case et al. | |
| 8,778,018 B2 | 7/2014 | Iobbi | |
| 2001/0002445 A1* | 5/2001 | Vesely | A61F 2/2409 623/2.11 |
| 2001/0007956 A1* | 7/2001 | Letac | A61F 2/2412 623/2.11 |
| 2001/0010017 A1 | 7/2001 | Letac et al. | |
| 2001/0021872 A1* | 9/2001 | Bailey | A61F 2/2418 623/1.24 |
| 2002/0032481 A1* | 3/2002 | Gabbay | A61F 2/2418 623/2.11 |
| 2002/0123802 A1* | 9/2002 | Snyders | A61F 2/2418 623/2.18 |
| 2002/0173842 A1 | 11/2002 | Buchanan | |
| 2003/0040792 A1 | 2/2003 | Gabbay | |
| 2003/0050694 A1 | 3/2003 | Yang et al. | |
| 2003/0100939 A1 | 5/2003 | Yodfat et al. | |
| 2003/0212454 A1 | 11/2003 | Scott et al. | |
| 2004/0030381 A1 | 2/2004 | Shu | |
| 2004/0186565 A1 | 9/2004 | Schreck | |
| 2005/0203616 A1 | 9/2005 | Cribier | |
| 2005/0234546 A1 | 10/2005 | Nugent et al. | |
| 2006/0149350 A1 | 7/2006 | Patel et al. | |
| 2006/0229719 A1 | 10/2006 | Marquez et al. | |
| 2009/0254177 A1* | 10/2009 | Yang | A61F 2/243 623/2.11 |
| 2014/0088697 A1 | 3/2014 | Fogarty et al. | |

FOREIGN PATENT DOCUMENTS

| | | | |
|---|---|---|---|
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0103546 A1 | 3/1984 | |
| EP | 0144167 A2 | 6/1985 | |
| EP | 0592410 A1 | 4/1994 | |
| EP | 0597967 A1 | 5/1994 | |
| EP | 0850607 A1 | 7/1998 | |
| EP | 1057460 A1 | 12/2000 | |
| EP | 1088529 A2 | 4/2001 | |
| EP | 1255510 A1 | 11/2002 | |
| EP | 1281375 A2 | 2/2003 | |
| EP | 1 356 793 A2 | 10/2003 | |
| EP | 1441672 A1 | 8/2004 | |
| EP | 1469797 A1 | 10/2004 | |
| EP | 1570809 A1 | 9/2005 | |
| FR | 2788217 A1 | 7/2000 | |
| GB | 2056023 A | 3/1981 | |
| SU | 1116573 A1 | 7/1985 | |
| SU | 1271508 A1 | 11/1986 | |
| WO | 91/17720 A1 | 11/1991 | |
| WO | 92/17118 A1 | 10/1992 | |
| WO | 93/01768 A1 | 2/1993 | |
| WO | 9640008 A1 | 12/1996 | |
| WO | 97/24080 A1 | 7/1997 | |
| WO | 98/29057 A1 | 7/1998 | |
| WO | 99/33414 A1 | 7/1999 | |
| WO | 99/40964 A1 | 8/1999 | |
| WO | 99/47075 A1 | 9/1999 | |
| WO | 00/41652 A1 | 7/2000 | |
| WO | 00/44313 A1 | 8/2000 | |
| WO | 00/47139 A1 | 8/2000 | |
| WO | WO 00/47139 A1 * | 8/2000 | A61F 2/2418 |
| WO | 01/35878 A2 | 5/2001 | |
| WO | 01/49213 A2 | 7/2001 | |
| WO | 01/62189 A1 | 8/2001 | |
| WO | 0154625 A1 | 8/2001 | |
| WO | 01/64137 A1 | 9/2001 | |
| WO | 01/76510 A2 | 10/2001 | |
| WO | 02/22054 A1 | 3/2002 | |
| WO | 02/36048 A1 | 5/2002 | |
| WO | 02/41789 A2 | 5/2002 | |
| WO | 02/43620 A1 | 6/2002 | |
| WO | 02/47575 A2 | 6/2002 | |
| WO | 02/49540 A2 | 6/2002 | |
| WO | 02076348 A1 | 10/2002 | |
| WO | 03011195 A2 | 2/2003 | |
| WO | 03/047468 A1 | 6/2003 | |
| WO | 2006/014233 A2 | 2/2006 | |
| WO | 2006/034008 A2 | 3/2006 | |
| WO | 2008/005405 A2 | 1/2008 | |
| WO | 2008/147964 A1 | 3/2008 | |
| WO | 0224118 A1 | 3/2008 | |
| WO | 2008/150529 A1 | 12/2008 | |

OTHER PUBLICATIONS

Andersen, Henning Rud, History of Percutaneous Aortic Valve Prosthesis, Herz 34, Aug. 2009, No. 5, Urban & Vogel, pp. 343-346, Skejby University Hospital Department of Cardiology, Aarhus, Denmark.

\* cited by examiner

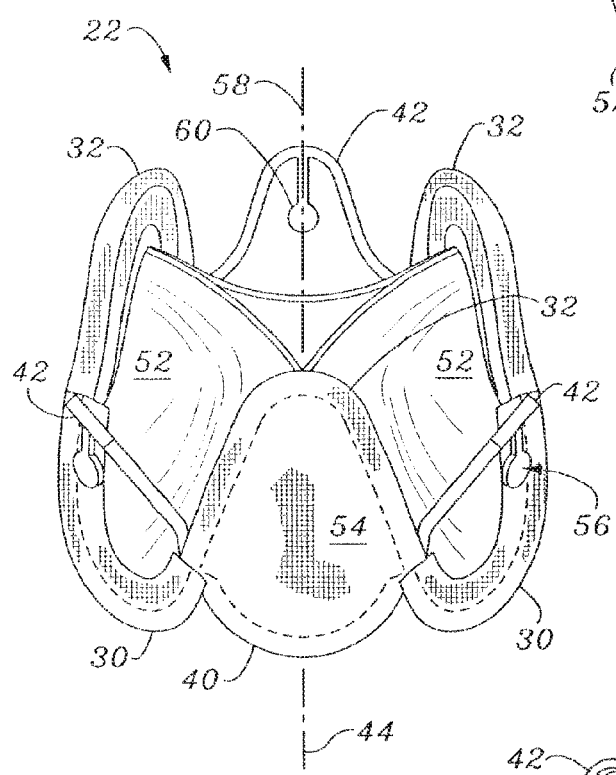
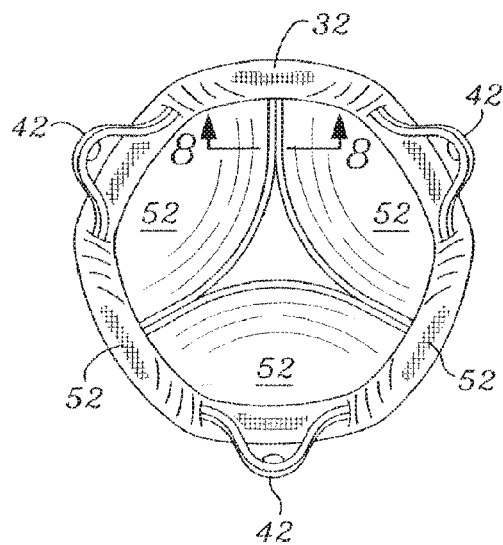
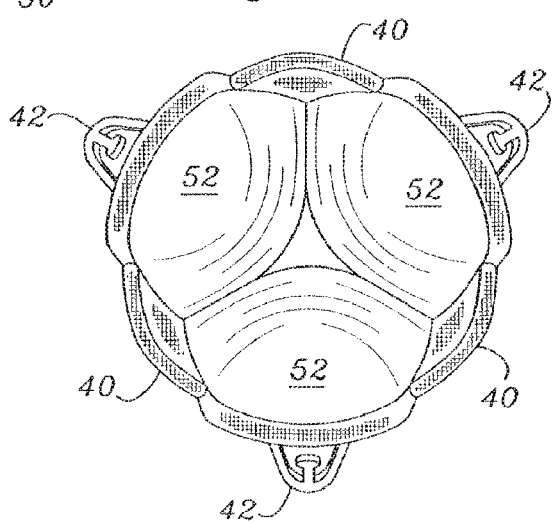

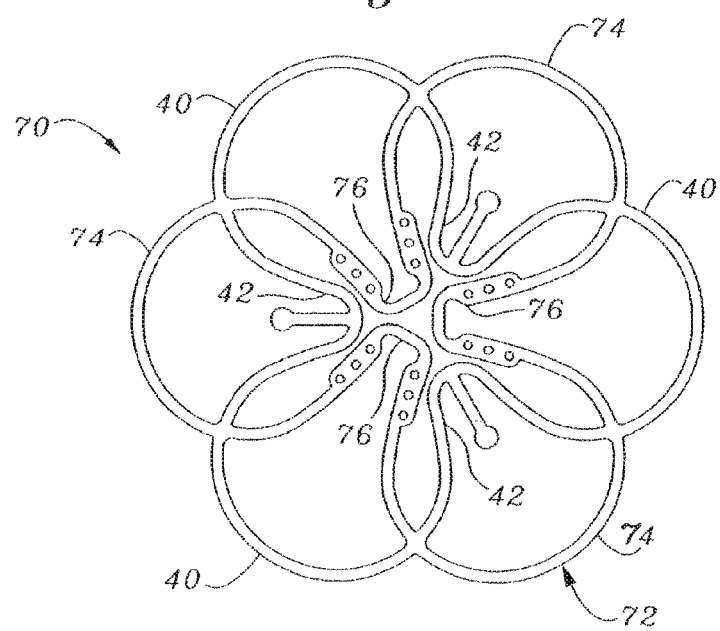
Fig. 4
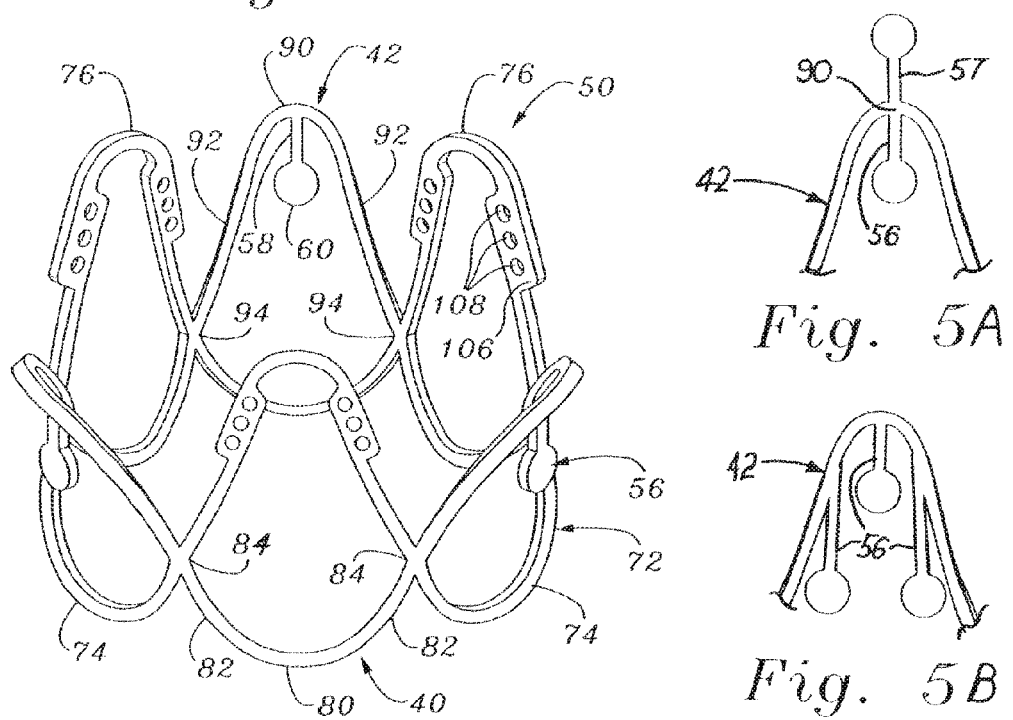
Fig. 5
Fig. 5A
Fig. 5B

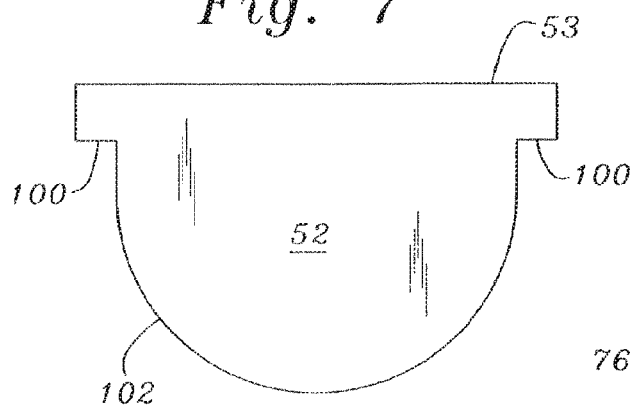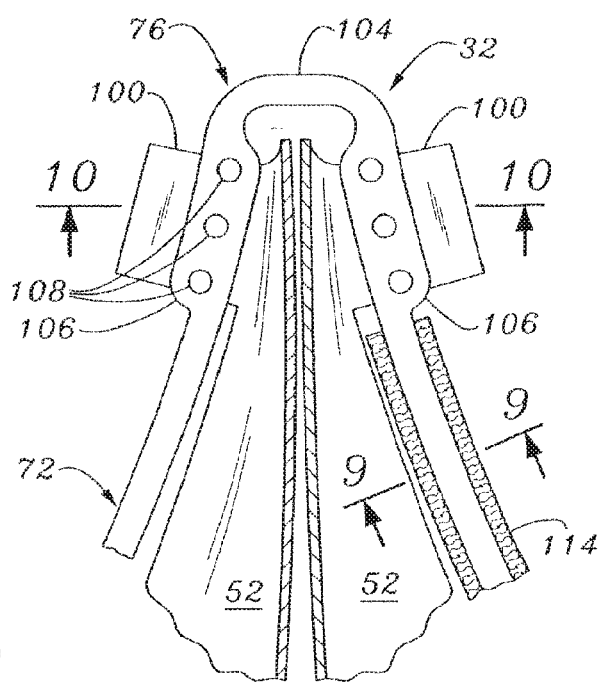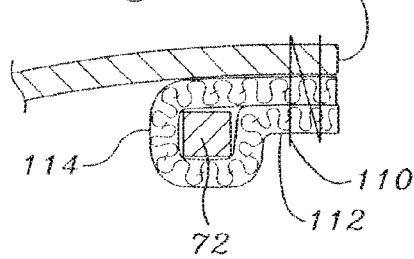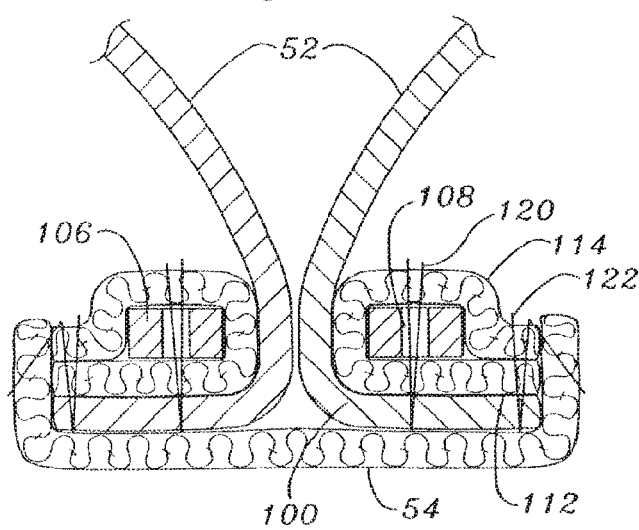

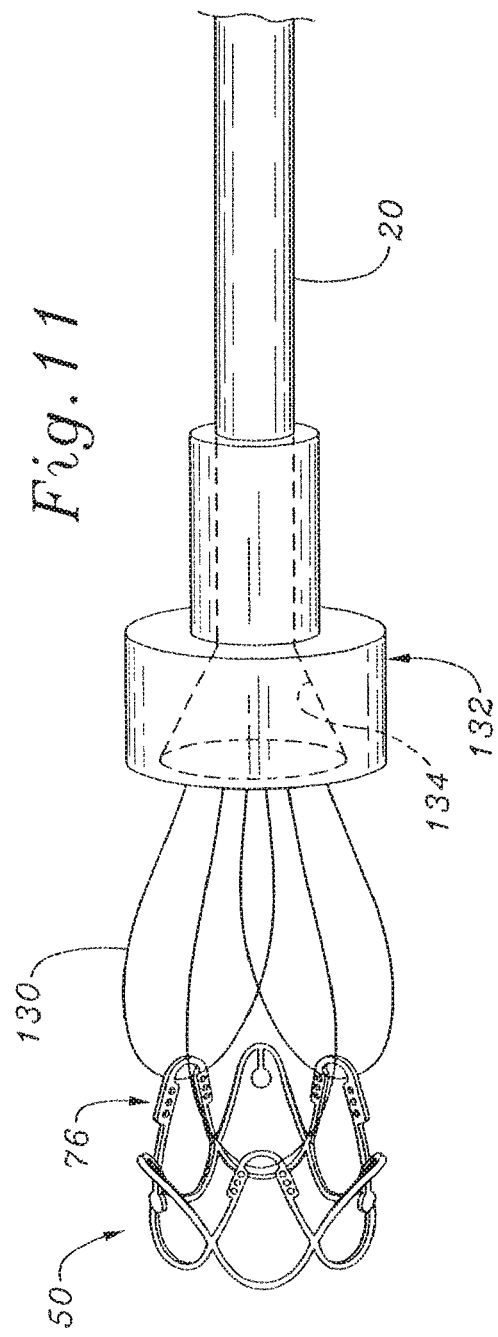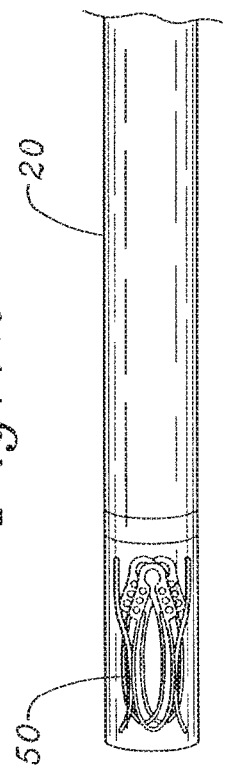

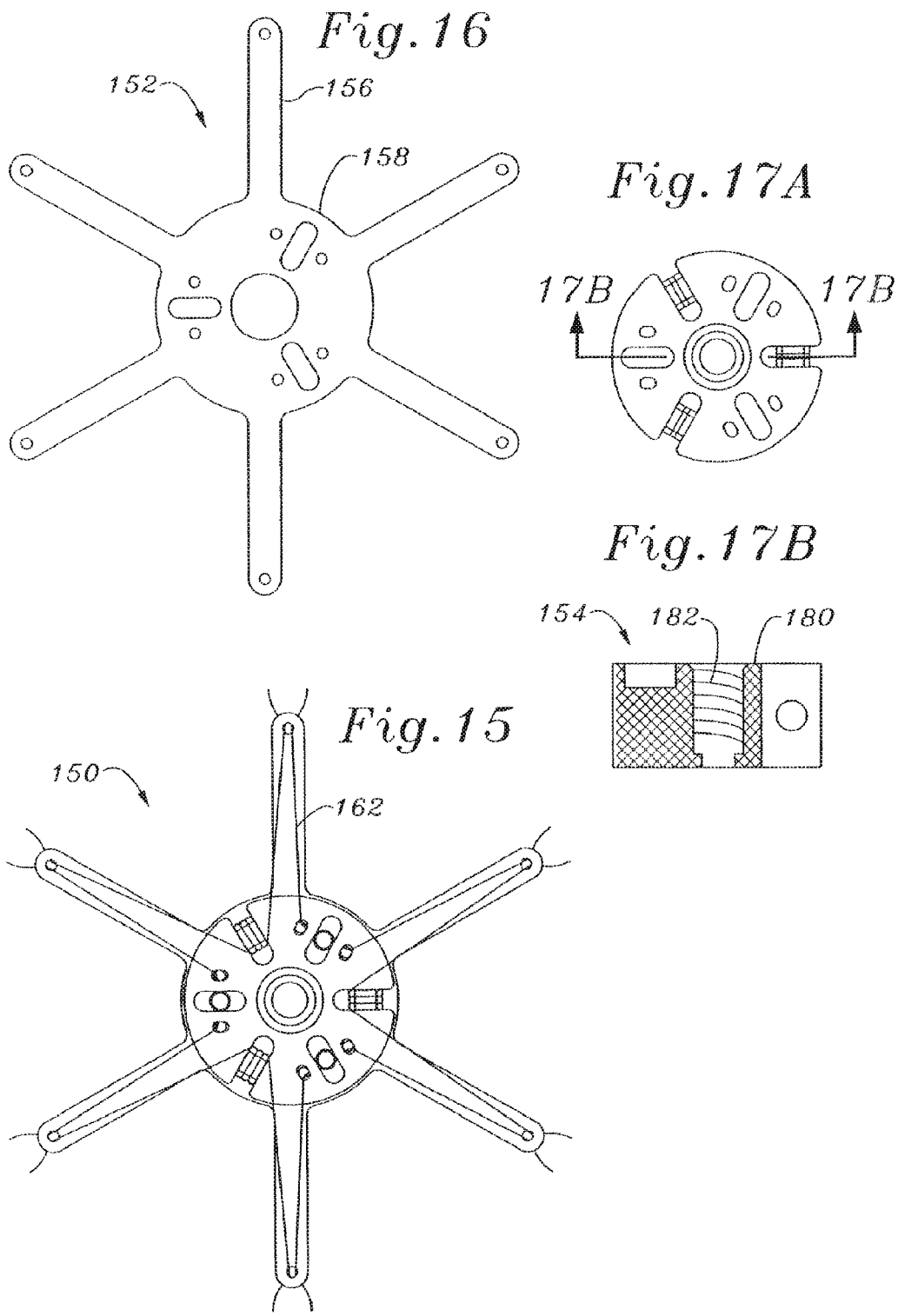

METHOD OF POSITIONING A MINIMALLY-INVASIVE HEART VALVE WITH CUSP POSITIONERS

RELATED APPLICATIONS

This application is a continuation of co-pending U.S. application Ser. No. 13/653,201, filed Oct. 16, 2012, which is a continuation of U.S. application Ser. No. 12/170,341, filed Jul. 9, 2008, now U.S. Pat. No. 8,778,018, which is a divisional of U.S. application Ser. No. 10/390,951, filed Mar. 18, 2003, now U.S. Pat. No. 7,399,315, all of which are incorporated herein by reference.

FIELD OF THE INVENTION

The present invention relates generally to medical implants, and more particularly to minimally-invasive or collapsible/expandable heart valves and methods of delivering and implanting such valves.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue or bioprosthetic-type valve. Bioprosthetic-type valves are often preferred over mechanical valves because they typically do not require long-term treatment with anticoagulants. The most common bioprosthetic-type valves are constructed with whole porcine (pig) valves, or with separate leaflets cut from bovine (cow) pericardium.

Although so-called stentless valves, comprising a section of xenograft (e.g., porcine) aorta and valve, are available, the most widely used valves include some form of artificial leaflet support. One such support is an elastic "support frame," sometimes called a "wireform" or "stent," which has a plurality (typically three) of large radius U-shaped cusps supporting the cusp region of the leaflets of the bioprosthetic tissue (i.e., either a whole valve or three separate leaflets). The free ends of each two adjacent cusps converge somewhat asymptotically to form upstanding commissures that terminate in U-shaped tips, each being curved in the opposite direction as the cusps, and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus. Therefore, the alternating cusps and commissures mimic the natural contour of leaflet attachment. Importantly, the wireform provides continuous support for each leaflet along the cusp region so as to better simulate the natural support structure.

The support frame is typically a non-ferromagnetic metal such as ELGILOY (a Co—Cr alloy) that possesses substantial elasticity. A common method of forming metallic support frames is to bend a wire into a flat (two-dimensional) undulating pattern of the alternating cusps and commissures, and then roll the flat pattern into a tube using a cylindrical roller. The free ends of the resulting three-dimensional shape, typically in the asymptotic region of the cusps, are then fastened together using a tubular splice that is plastically crimped around the ends. See FIGS. 3 and 4 of U.S. Pat. No. 6,296,662 for a support frame that is crimped together at a cusp midpoint.

Some valves include polymeric "support frames" rather than metallic, for various reasons. For example, U.S. Pat. No. 5,895,420 discloses a plastic support frame that degrades in the body over time. Despite some favorable attributes of polymeric support frames, for example the ability to mold the complex support frame shape, conventional metallic support frames are generally preferred for their elastic properties, and have a proven track record in highly successfully heart valves. For example, the CARPENTIER-EDWARDS Porcine Heart Valve and PERIMOUNT Pericardial Heart Valve available from Edwards Lifesciences LLC both have ELGILOY support frames and have together enjoyed the leading worldwide market position since 1976.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Some attempts have been made to enable less traumatic delivery and implantation of prosthetic heart valves. For instance, U.S. Pat. No. 4,056,854 to Boretos discloses a radially collapsible heart valve secured to a circular spring stent that can be compressed for delivery and expanded for securing in a valve position. Also, U.S. Pat. No. 4,994,077 to Dobbin describes a disk-shaped heart valve that is connected to a radially collapsible stent for minimally invasive implantation.

Recently, a great amount of research has been done to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still typically requires bypass, but the excision of the native valve and implantation of the prosthetic valve are accomplished via elongated tubes or cannulas, with the help of endoscopes and other such visualization techniques.

Some examples of more recent MIS heart valves are shown in U.S. Pat. No. 5,411,552 to Anderson, et al., U.S. Pat. No. 5,980,570 to Simpson, U.S. Pat. No. 5,984,959 to Robertson, et al., U.S. Pat. No. 6,425,916 to Garrison, et al., and PCT Publication No. WO 99/334142 to Vesely.

Although these and other such devices provide various ways for collapsing, delivering, and then expanding a "heart valve" per se, none of them disclose much structural detail of the valve itself. For instance, the publication to Vesely shows a tissue leaflet structure of the prior art in FIG. 1, and an expandable inner frame of the invention having stent posts in FIGS. 3A-3C. The leaflets are "mounted to the stent posts 22 in a manner similar to that shown in FIG. 1."

Likewise, Anderson describes mounting a porcine valve inside of an expandable stent "by means of a suitable number of sutures to form the cardiac valve prosthesis 9 shown in FIG. 2." Such general disclosures stop short of explaining how to construct a valve in a manner that maximizes long-term efficacy. In particular, the particular means of attaching the leaflets to the MIS stent is critical to ensure the integrity and durability of the valve once implanted. All of the prior art MIS valves are inadequate in this regard. Furthermore, use of conventional support stents or wireforms is difficult in MIS valves because of the need to compress the valve into a relatively small diameter delivery package, which creates material challenges.

Some MIS valves of the prior art are intended to be used without removing the natural valve leaflets. Sometimes the natural leaflets are heavily calcified, and their removal entails some risk of plaque particles being released into the bloodstream. Therefore, some of the MIS valves are designed to expand outward within the annulus and native leaflets, and compress the leaflets against the annulus. The relatively uneven surface of the calcified annulus and leaflets creates sizing problems and may complicate the delivery and placement steps. Prior art MIS valves are essentially tubular stents embellished with a native xenograft valve. The implant methodology is simply the conventional balloon expansion technique or pushing a self-expanding version from the end of a catheter. Minimal control over the placement of the valve is provided or contemplated.

Despite some advances in MIS valve design, there remains a need for an MIS valve that is durable and which has a more flexible delivery and implantation methodology.

SUMMARY OF THE INVENTION

The present invention provides improved prosthetic heart valves that can be implanted in a minimally-invasive manner, but which also has aspects that make it useful for conventional surgeries. The valves and implant tools and methods described herein provide a highly adaptive and simple to use endovascular delivery option for cardiac surgeons or cardiologists because of features that facilitate implantation. The valve is designed to be expelled from a delivery tube in an implant area and then expanded and/or positioned to contact the surrounding tissue without additional anchoring structures. Further, the valve and implant tools permit repositioning and even recollapse of the valve if needed.

In accordance with a first aspect of the invention, a prosthetic heart valve support frame comprises a leaflet frame and three cusp positioners. The leaflet frame has a continuous, undulating shape that mimics the natural fibrous structure of an aortic valve. The leaflet frame has three cusp regions alternating with and intermediate three commissure regions, the three cusp regions being positioned at an inflow end of the support frame and circumferentially about a flow axis defined within the support frame. The three commissure regions are positioned at an outflow end of the support frame and circumferentially about the flow axis. The three cusp positioners are rigidly fixed with respect to the leaflet frame and are disposed circumferentially about the flow axis. Each cusp positioner is located at the outflow end of the support frame and intermediate two of the commissure regions of the leaflet frame.

The leaflet frame and the cusp positioners may be formed integrally as a single piece. Desirably, the support frame is formed by a process comprising providing a two-dimensional blank of the support frame, and forming the two-dimensional blank into the three-dimensional heart valve support frame. The leaflet frame and the cusp positioners may be made of Nitinol, preferably with a martensitic transition temperature of less than about 5° C. and an austenitic transition temperature of more than about 20° C.

Each cusp positioner of the heart valve support frame desirably has a U-shape with an apex of the U-shape pointing toward the outflow end of the support frame and two legs of the U-shape pointing toward the inflow end. Each of the two legs of each U-shaped cusp positioner may be rigidly fixed to the continuous leaflet frame at a location approximately midway between a cusp region and a commissure region thereof. An anti-migration member such as an elongated section terminating in an enlarged and rounded head can be rigidly fixed to each cusp positioner to project therefrom. The cusp positioners may flare outwardly from the rest of the support frame to better contact surrounding tissue.

The support frame further may include three cusp connectors rigidly fixed with respect to the leaflet frame and disposed circumferentially about the flow axis. Each cusp connector is located at the inflow end of the support frame and intermediate two of the cusp regions of the leaflet frame. Each cusp connector desirably has a U-shape with an apex of the U-shape pointing toward the inflow end of the support frame and two legs of the U-shape pointing toward the outflow end. In a preferred embodiment, the leaflet frame, cusp positioners, and cusp connectors are formed integrally as a single piece, and the three cusp positioners and three cusp connectors define a continuous, undulating shape that generally mimics the shape of the leaflet frame but is rotated 60° about the flow axis therefrom.

Another aspect of the invention is a collapsible prosthetic heart valve that has a collapsible leaflet frame, three separate, flexible leaflets attached to the leaflet frame, and three cusp positioners rigidly fixed with respect to the leaflet frame. The leaflet frame has three cusp regions intermediate three commissure regions, the three cusp regions being positioned at an inflow end of the leaflet frame and circumferentially about a flow axis defined within the support frame. The three commissure regions are positioned at an outflow end of the leaflet frame and circumferentially about the flow axis. Each flexible leaflet has an arcuate cusp edge opposite a free edge and a pair of commissure edges therebetween. The leaflets attach around the leaflet frame with the cusp edge of each leaflet extending along one of the cusp regions, and a commissure edge of each leaflet meeting a commissure edge of an adjacent leaflet at one of the commissure regions. The three cusp positioners are rigidly fixed with respect to the leaflet frame and are disposed circumferentially about the flow axis, each cusp positioner being located at the outflow end of the leaflet frame and intermediate two of the commissure regions of the leaflet frame.

The heart valve may incorporate the aforementioned features of the support frame, for example a leaflet frame with a continuous, undulating shape that mimics the natural fibrous structure of an aortic valve, cusp connectors, and anti-migration members on each cusp positoiner. Desirably, an inflow periphery of the heart valve is defined along alternating and rigidly fixed cusp regions and cusp connectors. The inflow periphery may have an external fabric covering, and the heart valve may further includes a fabric panel defining an exterior surface of the heart valve between each pair of cusp positioner and cusp connector. Preferably, the leaflet frame has a fabric covering along substantially its entire length, the fabric covering defining a flange, and wherein the arcuate cusp edges of the flexible leaflets attach to the fabric covering flange. The fabric covering flange may project generally outward from the leaflet frame such that the cusp edges of the flexible leaflets extend radially outward past and underneath the leaflet frame to be sewn to the fabric covering flange. Each flexible leaflet may have a pair of tabs extending on either side of its free edge, wherein two tabs of adjacent flexible leaflets meet and pass together to the outside of the adjacent commissure region of the leaflet frame and are attached thereto using sutures through the tabs.

In accordance with a still further aspect of the invention, a collapsible prosthetic heart valve comprises:

a continuous, collapsible leaflet frame having three U-shaped cusp regions intermediate three U-shaped commissure regions, the three cusp regions being positioned at an inflow end of the leaflet frame and circumferentially about a flow axis defined within the leaflet frame, the three commissure regions being positioned at an outflow end of the leaflet frame and circumferentially about the flow axis;
   a cloth covering extending around the leaflet frame; and
   three separate, flexible leaflets attached to the leaflet frame, each leaflet having an arcuate cusp edge opposite a free edge and a pair of commissure edges therebetween, the leaflets being attached around the leaflet frame with the cusp edge of each leaflet extending along one of the cusp regions, and a commissure edge of each leaflet meeting a commissure edge of an adjacent leaflet at one of the commissure regions, the commissure edges of each leaflet further including a tab, wherein the tabs of two adjacent leaflets extend through the U-shape commissure region, diverge on the outside of commissure region, and are attached to the leaflet frame on the outside of the commissure region.

The present invention also encompasses a method of implanting a prosthetic aortic heart valve with a first step of providing a collapsible prosthetic heart valve having a collapsible leaflet frame defined by three cusp regions on an inflow end of the valve intermediate three commissure regions on an outflow end of the valve. The valve includes three cusp positioners on the outflow end and intermediate the three commissure regions. The method includes collapsing the prosthetic heart valve within a delivery tube, advancing the prosthetic heart valve within the delivery tube to an aortic annulus, expelling the prosthetic heart valve from the delivery tube by relative movement therebetween, expanding the prosthetic heart valve, and positioning the prosthetic heart valve such that the cusp positioners contact the two coronary and one non-coronary sinuses of the ascending aorta without blocking the coronary ostia.

The method preferably includes the step of connecting a holder having flexible members to the commissure regions of the prosthetic heart valve and utilizing the flexible members to perform the step of positioning the prosthetic heart valve. Flexible members of the holder may also be connected to the cusp positioners and utilized to perform the step of positioning the prosthetic heart valve, or to rotate the prosthetic heart valve during the step of positioning. Advantageously, the flexible members may be used to recollapse the prosthetic heart valve after the step of expanding. The prosthetic heart valve is desirably expanded in a location that is inferior to a final implant position such that the cusp positioners contact the surrounding aortic annulus, and the step of positioning comprises displacing the valve in a superior direction to a final implant position. The cusp positioners may be flared outward to define a circle about a flow axis of the valve greater than a circle about the flow axis defined by the three commissure regions, such that the step of displacing the valve in a superior direction causes the outwardly flared cusp positioners to be channeled into perspective coronary sinuses.

In accordance with a preferred method, the collapsible leaflet frame is formed of a shape memory alloy having a martensitic transition temperature less than room temperature and an austenitic transition temperature less than body temperature, and the step of collapsing is done with the material of the leaflet frame at a temperature less than its martensitic transition temperature. For example, the step of collapsing may be done in conjunction with immersing the prosthetic heart valve in an ice bath to reduce the temperature of the material of leaflet frame to below its martensitic transition temperature. In another aspect, the collapsible leaflet frame may be formed of a shape memory alloy having a memory condition in its expanded state, and wherein the step of expanding the prosthetic heart valve comprises both permitting self-expansion of the valve to an intermediate diameter and then using a physical expander to increase the diameter of the valve to the memory condition of the leaflet frame.

A further method of implanting a collapsible prosthetic heart valve provided by the present invention comprises first providing a self-expanding valve comprised of a material displaying hysteresis in the elastic or superelastic region. The valve is permitted to self-expand to a first diameter, and then the valve is assisted with a physical expander such as a balloon to further expand to a second diameter.

The prosthetic heart valve may includes a collapsible leaflet frame formed of a shape memory alloy having a martensitic transition temperature less than room temperature and an austenitic transition temperature less than body temperature, and the method may further include a step of collapsing the valve with the material of the leaflet frame at a temperature less than its martensitic transition temperature. Fir example, the step of collapsing may be done in conjunction with immersing the prosthetic heart valve in an ice bath to reduce the temperature of the material of leaflet frame to below its martensitic transition temperature.

The prosthetic heart valve may have a collapsible leaflet frame defined by three cusp regions on an inflow end of the valve intermediate three commissure regions on an outflow end of the valve, and three cusp positioners on the outflow end and intermediate the three commissure regions. In this case, the method may further include:

collapsing the prosthetic heart valve within a delivery tube;
   advancing the prosthetic heart valve within the delivery tube to an aortic annulus;
   expelling the prosthetic heart valve from the delivery tube by relative movement therebetween;
   expanding the prosthetic heart valve by the steps of permitting self-expansion and assisting further expansion; and
   positioning the prosthetic heart valve such that the cusp positioners contact the two coronary and one non-coronary sinuses of the ascending aorta without blocking the coronary ostia.

BRIEF DESCRIPTION OF THE DRAWINGS

FIGS. 3A-3C are perspective, top plan, and bottom plan views, respectively, of the prosthetic heart valve of FIG. 2A;

FIG. 4 is a plan view of a prosthetic heart valve support frame of the present invention in a two-dimensional blank form prior to conversion to three-dimensional final form;

FIG. 5 is a perspective view of the prosthetic heart valve support frame of FIG. 4 in its three-dimensional final form with a leaflet frame and cusp positioners;

FIGS. 5A and 5B are views of a portion of the three-dimensional heart valve support frame of FIG. 5 showing alternative cusp positioner configurations;

FIG. 7 is a plan view of an exemplary leaflet used in the prosthetic heart valves of the present invention;

FIG. 8 is a partial sectional view of a commissure region of the exemplary prosthetic heart valve taken along line 8-8 of FIG. 3B;

FIG. 9 is a sectional view through a portion of the support frame of the exemplary prosthetic heart valve, taken along line 9-9 of FIG. 8;

FIG. 10 is a sectional view through a commissure tip region of the exemplary prosthetic heart valve, taken along line 10-10 of FIG. 8;

FIG. 11 is a schematic perspective view of a prosthetic heart valve support frame of the present invention being loaded into a delivery catheter;

FIG. 12 is a perspective view of the support frame after having been loaded into a delivery catheter;

FIG. 15 is a bottom plan view of an exemplary compressible/expandable heart valve holder of the present invention;

FIG. 16 is a plan view of a multi-armed flexible portion of the holder of FIG. 15; and FIGS. 17A-17B are two views of a rigid portion of the holder of FIG. 15.

DESCRIPTION OF THE PREFERRED EMBODIMENTS

Figure 1:
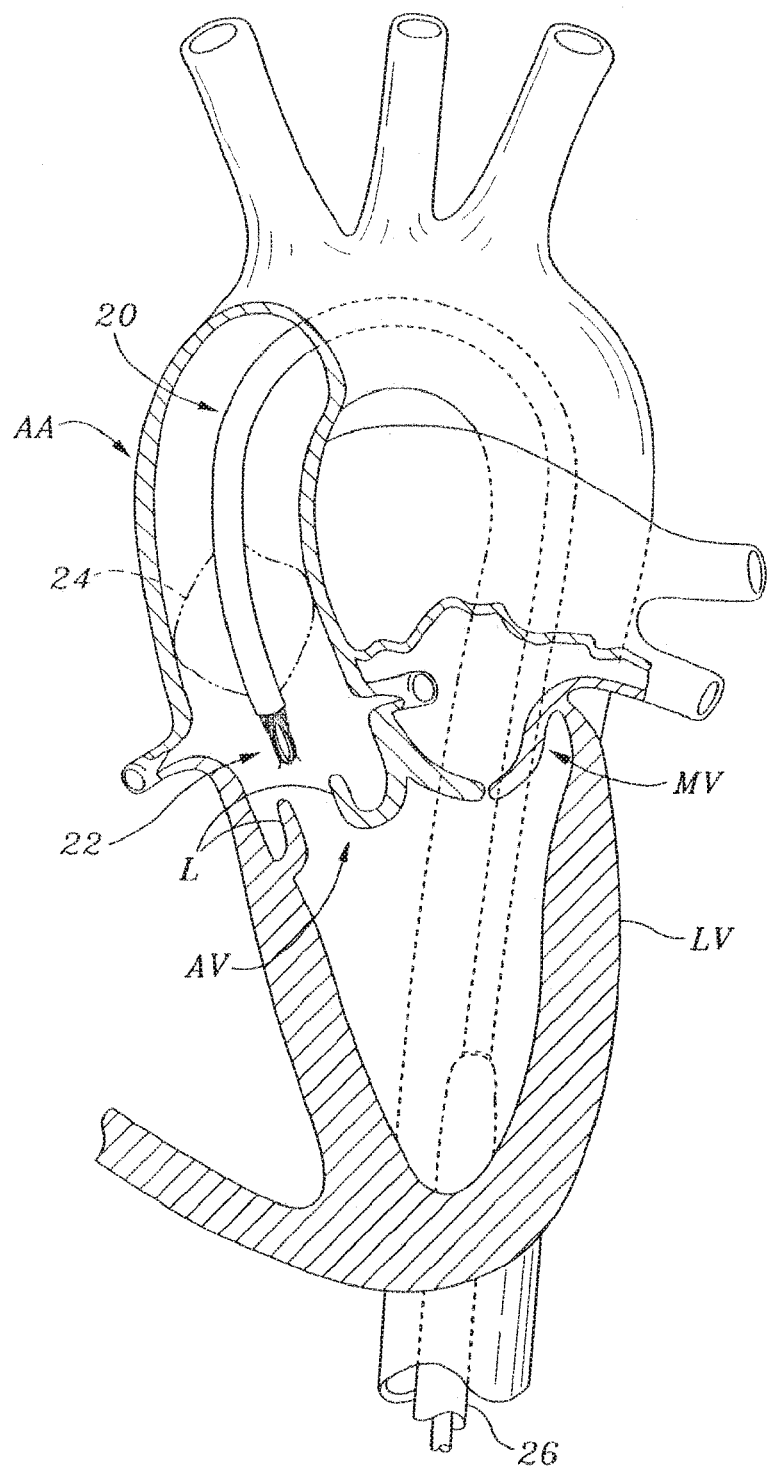
FIG. 1 is a partial view of a patient's heart generally vertically section through the left ventricle and associated heart valves, and illustrating the implantation approach of a catheter-based prosthetic valve of the present invention.

The present invention provides an improved minimally invasive (MIS) valve support frame, MIS valve, and methods of construction and delivery as described herein and shown in the accompanying drawings.

The invention pertains primarily to flexible leaflet heart valves and internal support frames, which are also referred to in the art as stents or wireforms. As mentioned above, the flexible leaflets can be formed from biological (e.g., bovine pericardium) or synthetic material. In this context, a "support frame" for a flexible leaflet heart valve provides the primary internal structural support for the leaflets, and substantially mimics the natural fibrous skeleton of the respective valve annulus. More specifically, each of the leaflets has an outer edge that is coupled to a portion of the support frame such that its inner edge is free to move within the orifice area of the valve, thus providing the opening and closing surfaces thereof. A biological xenograft valve can be used to provide the flexible leaflets in the valves of the present invention, though the internal support frame is particularly suited to receive individual leaflets.

The leaflet frames of the present invention have a continuous, undulating shape with three arcuate or U-shaped cusp regions on the inflow end separated by three upstanding and generally axially-oriented arcuate or U-shaped commissure regions on the outflow end. Around the circumference of the leaflet frame, the shape has an alternating structure of cusp-commissure-cusp-commissure-cusp-commissure, and generally describes a conical surface of revolution with the three commissures on the outflow end of the valve being closer together than the three cusps. Some support frames may alternatively describe a tubular surface of revolution about an axis. The cusp regions and commissure regions are evenly distributed about a flow axis through the support frame, and therefore the three cusp regions are 120° apart from each other, and each of the three commissure regions is 120° apart from the next and 60° from the adjacent cusp regions.

The term "continuous" to describe the heart valve leaflet frame means that a single continuous and closed-shape line (i.e., loop) can be drawn following the sequential cusp and commissure regions, and "undulating" refers to the serpentine or alternating sinusoidal character of the line. More generally, a continuous, undulating heart valve leaflet frame approximates the shape of the natural fibrous tissue around the aortic valve annulus so as to mimic that natural support structure for optimum functionality of the prosthetic leaflets.

The present invention primarily pertains to prosthetic heart valves suitable for minimally invasive delivery and implantation. Such minimally invasive valves are capable of being compressed or collapsed into a small profile and delivered through a catheter or cannula (a tube) to the site of implantation for remote expansion and anchoring thereto. It should be understood, however, that certain aspects of the invention described herein are beneficial for prosthetic heart valves in general, and thus not all of the claims should be construed to require a minimally invasive valve.

FIG. 1 depicts a portion of a heart of a patient with the left ventricle LV, aortic valve AV, mitral valve MV, and ascending aorta AA shown in section. A delivery catheter or tube 20 is seen in position just prior to complete expulsion and expansion of a prosthetic heart valve 22 from a distal end thereof for implant at the aortic valve AV annulus. The aortic valve AV leaflets L may first be excised prior to implant of the valve 22, or more preferably the leaflets L remain in place and are expanded outward and compressed against the lumen of the aortic valve AV annulus upon expansion of the valve. The distal end of the delivery tube 20 may optionally be stabilized by a balloon 24 (shown in phantom) inflated against the lumen of the ascending aorta AA, or through other means. The delivery tube 20 is preferably inserted in the vasculature of the patient using a larger diameter introducer 26 through a peripheral vessel such as the femoral artery or femoral vein. Alternatively, the peripheral vessel may be the internal jugular vein, the subclavian artery, the axillary artery, the abdominal aorta, the descending aorta, or any other suitable blood vessel. The introducer 26 may be inserted by surgical cut down or percutaneously using the Seldinger technique.

Figure 2B:
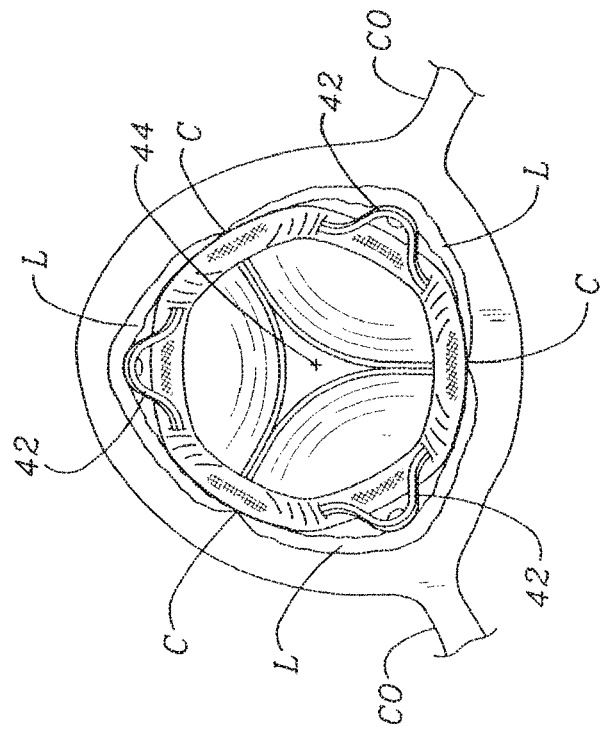
FIG. 2B is a top plan view of the implanted prosthetic heart valve of FIG. 2A.
Figure 2A:
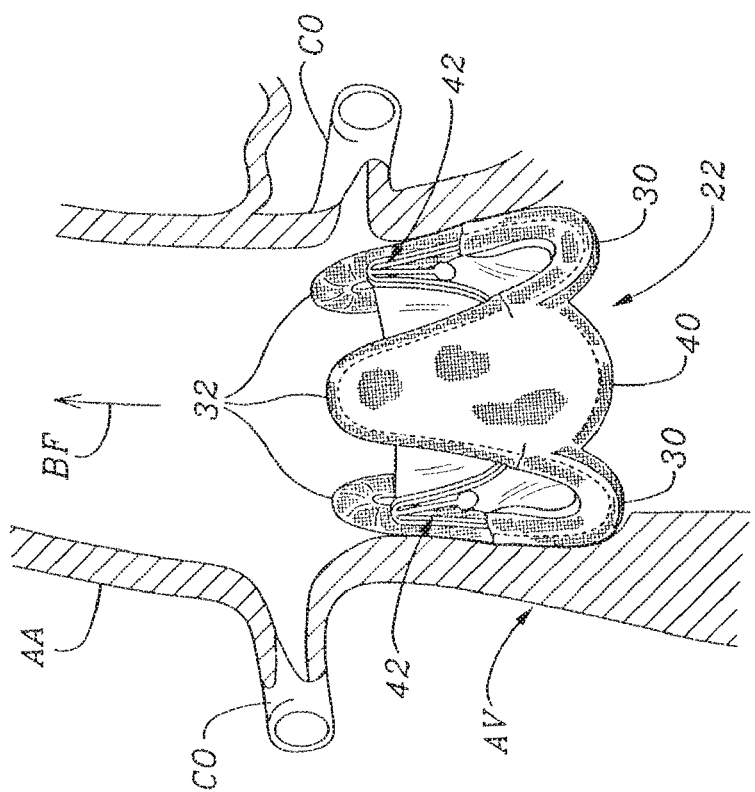
FIG. 2A is a vertical sectional view through an aortic annulus and an exemplary prosthetic heart valve of the present invention implanted therein.

FIGS. 2A and 2B illustrate the prosthetic heart valve 22 implanted at the aortic valve AV annulus. The heart valve 22 includes three cusps 30 on an inflow end (one of which is not visible) and three commissures 32 on an outflow end. The direction of blood flow BF is indicated with an arrow in the ascending aorta AA. The natural leaflets are desirably compressed against the lumen of the aortic valve annulus by the prosthetic heart valve 22, as seen in FIG. 2B. The valve 22 is oriented about a flow axis such that the commissures 32 are generally aligned with the native commissures C, while the cusps (not shown but intermediate the commissures 32) are generally aligned with the natural cusps/leaflets L. The heart valve 22 contacts the lumen wall of the aortic valve AV annulus and desirably retains its position due to friction therebetween. In this regard, the heart valve 22 expands from its delivery configuration shown in FIG. 1 to the expanded configuration in FIGS. 2A and 2B.

The valve 32 contacts the lumen wall around the entire periphery of the inflow end thereof and in certain areas adjacent to the inflow periphery, as will be explained below. The inflow periphery is defined by the lower ends of the cusps 30 as well as by the lower ends of three cusps connectors 40 that extend between and fill the gaps between the cusps 30. Additionally, the heart valve 22 includes three cusp positioners 42, two of which are visible in FIG. 2A, that are rigidly fixed with respect to an internal valve support frame and are each located generally at the outflow end of the valve intermediate two of the commissures 32. With reference to FIG. 2B, the cusp positioners 42 are evenly distributed about a central flow axis 44, and when implanted align with the native leaflets L. The cusp positioners 42 preferably extend radially farther outward than the commissures 32 and compress the leaflets L against the natural sinus cavities formed just above the aortic valve AV annulus. Coronary ostia CO open from two of the three sinus cavities, as seen in FIG. 2A, and the cusp positioners 42 are sized and placed by the operator to avoid occluding flow through the coronary ostia CO. The advantageous structure and function of these cusp positioners 42 will be more fully explained below.

With reference now to FIGS. 3A-3C, the exemplary prosthetic heart valve 22 will be more fully described. The shape of an internal support frame 50 seen in FIG. 5 generally governs the shape of the valve 22. As mentioned, the valve 22 includes the aforementioned cusps 30 and commissures 32 evenly distributed about a flow axis 44. The cusps 30 and cusp connectors 40 define a scalloped inflow periphery of the valve 22, while the outflow periphery is defined by the three commissures 32 and the three cusp positioners 42. The entire internal support frame 50 except for the cusp positioners 42 is covered over with one or more layers of material, the exterior layer of which is typically a fabric as shown (but not numbered). The use of a fabric such as polyethylene terephthalate provides a matrix into which surrounding tissue can grow to help anchor the valve in place.

Three flexible leaflets 52 mount to the valve 22 in a trifoil configuration with free edges 53 thereof arranged to meet or coapt in the middle of the valve and provide one-way occlusion. An outer edge of each leaflet 52 attaches to the valve 22 between two of the commissures 32 and around one of the cusps 30. An exemplary structural attachment of the leaflets 52 to the internal support frame 50 will be described below.

As mentioned, each cusp connector 40 extends between two of the cusps 30. A panel of fabric or other material 54 covers an area between the inflow or lower edge of each cusp connector 40 and the corresponding commissures 32. Some of this panel of fabric 54 desirably contacts the lumen wall of the aortic valve AV annulus to help prevent leakage around the valve.

The exemplary cusp positioners 42 each have an inverted U-shape with an apex pointed toward the outflow end of the valve 22 and two legs extending generally toward the inflow end and connecting with the remainder of the valve. The term "U-shape" is intended to cover all configurations that have two legs and an apex therebetween. Other figurative descriptions such as V-shaped, bell-shaped, sinusoidal, arcuate, or the like are therefore encompassed by the term "U-shape". It is contemplated, however, that the cusp positioners 42 could assume other forms, such as a generally linear, cantilevered arm extending upward from the midpoint of each cusp 30. In whatever form, the cusp positioners 42 provide the valve 22 with three points of contact with the surrounding tissue that is midway between the three commissures 32 so as to help stabilize and anchor the valve in its implant position. Moreover, the cusp positioners 42 desirably perform the function of compressing the native leaflets L outward against the sinus cavities, at least in those procedures where the leaflets L are not excised.

The leaflets L in a diseased valve may be less than flexible, and indeed may be highly calcified. It is often considered preferable to avoid removing the leaflets L so as to avoid disturbing the calcification or other stenotic material that has built up around the leaflets. Therefore, the present invention desirably provides structure to compress the native leaflets L outward against the aortic wall sinus cavities and hold the leaflets in that position so as to avoid flapping and potentially interfering with blood flow through the prosthetic valve. The inverted U-shape of the cusp positioners 42 is believed to provide effective structure to both anchor the valve in the aortic valve AV annulus and also control, or corral, if you will, the obsolete native leaflets L. At the same time, the cusp positioners 42 are relatively minimal in total area so as to avoid unduly interfering with back flow of blood on the outflow side of each of the leaflets 52, or to the coronary ostia CO. Therefore, the cusp positioners 42 are desirably defined by relatively thin members, as shown, as opposed to walls or panels, or the like. Multiple cusp positioners 42 per valve cusp 30 are conceivable, though the total solid volume taken up by the cusp positioners should be kept to a minimum so as to minimize the risk of occluding the coronary ostia CO.

Figure 6A:
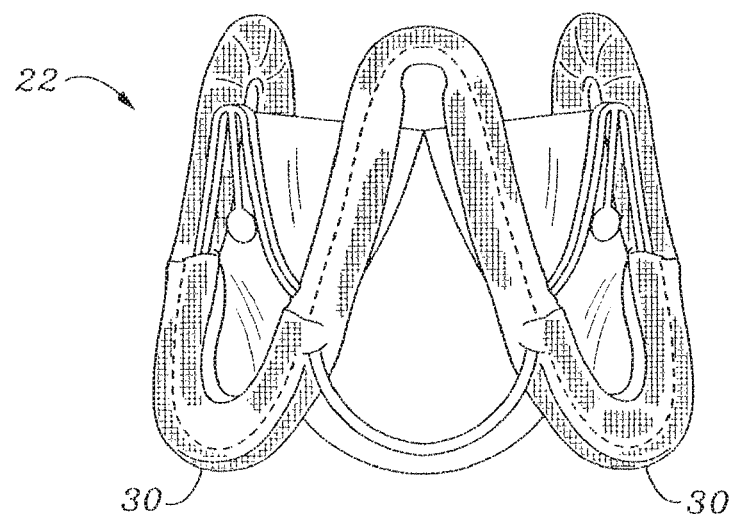
FIG. 6A is an elevational view of a partially assembled prosthetic heart valve as in FIGS. 3A-3C.
Figure 6B:
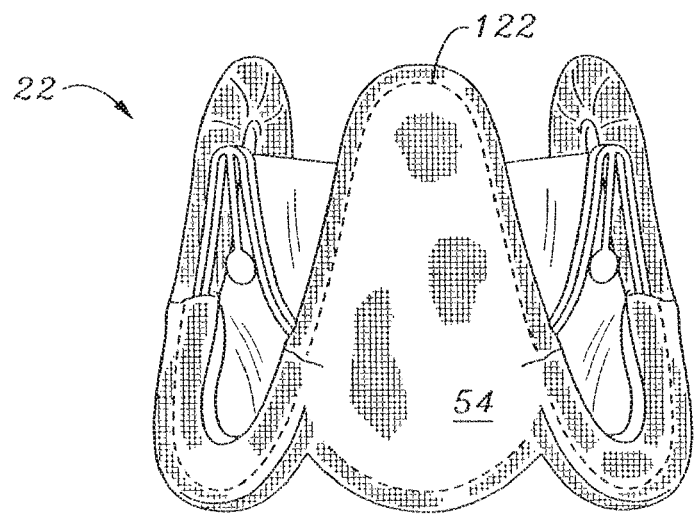
FIG. 6B is an elevational view of the prosthetic heart valve of FIG. 6A fully assembled.
Figure 13A:
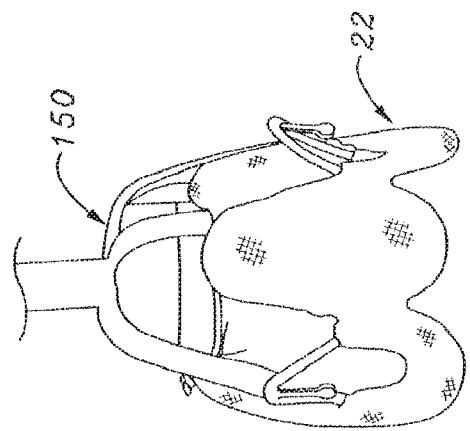
FIGS. 13A-13B are perspective and elevational views of an exemplary compressible/expandable heart valve holder attached to a prosthetic heart valve of the present invention.

The axial height of the cusp positioners 42 relative to the commissures 32 is seen best in FIG. 2A (and in FIG. 6B). Preferably, the commissures 32 are slightly taller than the cusp positioners 42, although such an arrangement is not considered mandatory. The main consideration in the size of the cusp positioners 42 is to avoid occluding the coronary ostia CO. Therefore, as seen in FIG. 2A, the cusp positioners 42 contact the surrounding aortic valve AV lumen wall just below the coronary ostia CO. Of course, the anatomy of each patient differs slightly from the next, and the precise position of the coronary ostia CO cannot be predicted with absolute certainty. Furthermore, the final location of the cusp positioners 42 is dependent on the skill of the cardiac surgeon or cardiologist. In the ideal situation, however, the cusp positioners 42 are positioned just below and aligned circumferentially with the coronary ostia CO as seen in FIGS. 2A and 2B.

FIGS. 2B and 3B-3C illustrate the relative outward radial position of the cusp positioners 42 with respect to the commissures 32 therebetween, and with respect to the cusp connectors 40. As seen in the isolated view of the heart valve support frame 50 in FIG. 5, the cusp positioners 42 are angled or flared outward from the remainder of the support frame. This outward flaring helps ensure good contact between the apex of the cusp positioners 42 and the surrounding walls of the aortic valve AV sinus cavities. In this regard, the outer configuration of the heart valve 22 is designed to maximize contact with the aortic valve AV lumen wall both in the annulus and for a short distance into each sinus cavity. This extensive surface contact between the prosthetic valve 22 and the surrounding tissue may obviate the need for sutures, staples, sharp barbs or other such anchoring structure, although such structure could be used in conjunction with the valve. The valve 22 is merely expelled from the end of the delivery tube 20 (FIG. 1), expanded with or without assistance of a balloon, and held in place by frictional contact between the inflow periphery against the annulus, and between the cusp positioners 42 and the sinus cavities (or intervening native leaflets).

Each cusp positioner 42 further includes at least one anti-migration member 56 rigidly fixed thereto and designed to help anchor the support frame 50 to the surrounding tissue. In the illustrated embodiment, the anti-migration members 56 each preferably includes an elongated section 58 terminating in an enlarged and rounded head 60, the configuration thus somewhat resembling a spoon. The anti-migration member 56 desirably projects out of the plane defined by the associated cusp positioner 42, and may extend generally axially in the inflow direction from the apex thereof, as seen in FIG. 3A. When the valve 22 is implanted, the anti-migration members 56 are designed to contact and become somewhat entrapped in the native leaflets. Therefore, the anti-migration members 56 act as a rounded barb of sorts to maintain the valve 22 in its implant position. The members 56 also may help prevent flapping of the native leaflets in the swirling blood flow. Numerous other configurations are contemplated, the general idea being that the anti-migration member 56 enhances the ability of the associated cusp positioner 42 to anchor to the surrounding tissue. In this regard, the term "anti-migration member" is meant to include any structure that enhances such anchoring, including both blunt and sharp structures (i.e., barbs).

Various procedures and apparatuses for converting a two-dimensional blank such as shown in FIG. 4 to the three-dimensional form of FIG. 5 are described in more detail in co-pending U.S. patent application Ser. No. 10/251,651, filed Sep. 20, 2002, and entitled continuous heart valve support frame and method of manufacture. In short, the process involves bending the two-dimensional blank 70 around a cylindrical or conical mandrel and altering the material so as to retain its three-dimensional shape. For example, various nickel-titanium alloys (Nitinol) may be easily bent around a mandrel and then set into that shape using heat treatments.

In an exemplary embodiment of the present invention, the internal support frame 50 of the valve 22 is made of a material that is highly flexible so as to permit maximum relative movement between the valve cusps and commissures, and in some cases to permit constriction into a small profile diameter for minimally invasive delivery to an implantation site. At the same time the support frame must possess a minimum amount of stiffness to provide the desired support to the leaflets. Therefore, there is a balance obtained between the requisite flexibility and stiffness.

The material for the internal support frame is desirably "elastic," which means that it has the capacity to rebound from imposed strain. Various NITINOL alloys are especially suitable for making the internal support frame of the present invention as in certain circumstances they are considered to be "superelastic." Other materials that may be used include ELGILOY, titanium, stainless-steel, even polymers, and similar expedients. These latter materials do not display superelasticity but are still elastic. Other materials may fit within this definition but they must be suitable for long-term implantation in the body.

The term "superelastic" (sometimes "pseudoelastic") refers to that property of some materials to undergo extreme strains (up to 8%) without reaching their failure stress limit. Some so-called shape memory alloys (SMAs) are known to display a superelastic phenomena or rubber-like behavior in which a strain attained beyond the elastic limit of the SMA material during loading is recovered during unloading. This superelastic phenomenon occurs when load is applied to an austenitic SMA article which first deforms elastically up to the yield point of the SMA material (sometimes referred to as the critical stress). Upon the further imposition of load, the SMA material begins to transform into stress-induced martensite or "SIM." This transformation takes place at essentially constant stress, up to the point where the SMA material is completely transformed into martensite. When the stress is removed, the SMA material will revert back into austenite and the article will return to its original, pre-programmed programmed or memorized shape.

The support frame 50 is desirably constructed of a material that exhibits hysteresis in the elastic and/or superelastic region. "Hysteresis" indicates that when the material is strained beyond the "memory condition" (defined as unconstrained geometry) it produces a stress-strain curve that is different and higher than the stress-strain curve produced as the material attempts to return to its memory condition. An example of a material that exhibits such a hysteresis is NITINOL. The presence of this hysteresis implies that it requires a greater force to displace the material form its memory condition than the material exerts as it recovers to its memory condition.

When using NITINOL the shape set is done at a particular temperature for a period of time designed to ensure certain properties in the material. Namely, the martensitic transition temperature is desirably less than room temperature and the austenitic transition temperature is desirably less than body temperature. For instance, the temperature below which the material is in martensitic form is around 0-5° C., while the temperature above which the material is in austenitic form is around 20-25° C. When the material is shape set in this way, the heart valve 22 can be cooled, such as in an ice bath, just prior to implant to change the crystalline structure of the support frame 50 to martensite and create high flexibility so as to enable compaction thereof into a small diameter delivery profile. After implant and expansion, the temperature rises from body heat above the austenitic transition temperature and thus the support frame 50 possesses the desired degree of stiffness to properly support the leaflets.

The support frame 50 (and blank 70) includes a leaflet frame 72 defined by three cusp regions 74 intermediate three commissure regions 76. In FIG. 4 the leaflet frame 72 in the blank 70 exhibits a three-leaf clover shape, while in FIG. 5 the leaflet frame 72 has a continuous, undulating shape as described above. A second three-leaf clover shape can be seen in FIG. 4 formed by the three cusp connectors 40 and three cusp positioners 42. When bent into the three-dimensional configuration of FIG. 5, two continuous, undulating shapes can be seen oriented 60° with respect to one another about the central flow axis. Each cusp connector 40 includes an apex 80 and a pair of legs 82 that rigidly attach to the leaflet frame 72 at junction points 84. Likewise, each cusp positioner 42 includes an apex 90 and a pair of legs 92 that rigidly attach to the leaflet frame 72 at junction points 94. In the preferred and illustrated embodiment, the junction points 84 and 94 are coincident.

FIGS. 5A and 5B show alternative cusp positioner configurations for the three-dimensional heart valve support frame 50 of FIG. 5. As mentioned above, the anti-migration members facilitate anchoring of the support frame 50 to the surrounding anatomy, and prevent axial and rotational movement of the valve 22. The anti-migration members 56 shown in FIG. 5 project generally axially in the inflow direction from the apex 90 of each cusp positioner 42. In FIG. 5A, a second anti-migration member 57 projects generally axially in the outflow direction from the apex 90 of each cusp positioner 42. In FIG. 5B, there are multiple anti-migration members 56 extending generally axially in the inflow direction. Various combinations, placements and orientations of these examples are contemplated, and the examples should not be considered limiting.

FIG. 6A shows the valve 22 almost completely assembled, but without the aforementioned cloth covers 54 that are seen in the fully assembled valve of FIG. 6B. The covers 54 help prevent leakage of blood around the implanted valve 22, and specifically in the areas between each pair of cusps 30.

FIG. 7 illustrates an exemplary leaflet 52 in plan view. The free edge 50 is shown as linear, but may also be arcuate, angled, trapezoidal, or other configuration. Each leaflet includes a pair of opposed generally rectangular tabs 100 at either end of the free edge 53. An arcuate cusp edge 102 extends between the tabs 100 and opposite the free edge 53. The tabs 100 and arcuate cusp edge 102 are secured to the valve 22, and specifically along the contours of the leaflet frame 72 seen in FIG. 5.

FIG. 8 is an enlarged cutaway view of one of the commissures 32 of the valve 22 taken along line 8-8 of FIG. 3B and showing the internal construction thereof. The commissure region 76 of the leaflet frame 72 tapers down in the outflow direction to a closed tip 104. Attachment flanges 106 are formed adjacent the tip 104 and desirably include a plurality of assembly holes 108 sized to permit passage of sutures therethrough. The adjacent leaflets 52 come together in the commissure regions 76 and the tabs 100 thereof are folded away from each other on the exterior of the flanges 106.

As seen in FIG. 9, the cusp edge 102 of each leaflet 52 attaches with sutures 110 to a cloth flange 112 of a tubular fabric cover 114 around the leaflet frame 72. This configuration causes tensile forces imparted by the leaflets 52 to be transferred as much as possible to the frame 72 rather than being primarily borne by the attachment sutures 110.

FIG. 10 shows the attachment structure at the commissure tip 104, and specifically illustrates sutures 120 passing through the fabric cover 114, through the assembly holes 108, and through the folded leaflet tabs 100. A second suture 122 passes through the cloth flange 112, the leaflet tab 100, and cloth covers 54 (also shown in FIG. 6B). Because each of the leaflets 52 includes the tab 100 that extends to the outside of the leaflet frame 72, high forces that are seen with closing of the valve are less likely to pull the sutures 120 through the tabs. That is, the construction shown in FIG. 10 causes tensile forces imparted by the leaflets 52 to be transferred as much as possible from the sutures 120, 122 to the frame 72, thus helping to prevent tearing of the flexible leaflets and rendering the valve 22 more durable.

FIGS. 11 and 12 schematically illustrate a technique for loading a prosthetic heart valve of the present invention into a delivery tube. For the sake of clarity, only the support frame 50 is shown being loaded into the delivery tube 20. A plurality of sutures or other such flexible members or filaments 130 are shown looped through each of the commissure regions 76 of the support frame 50. These filaments 130 extend into the distal end of the delivery tube 20 and through its lumen to a proximal end (not shown) where they are connected to a tensioning device. In actual use, the filaments 130 would be threaded through the commissures 32 of the valve 22, avoiding the flexible leaflets. A loading adapter 132 couples to the distal end of the delivery tube 20. The adapter 132 includes an inner funnel-shaped opening 134. Tension on the filaments 130 pulls the commissures 32 of the valve into the funnel-shaped opening 134 which gradually compresses the valve into a diameter smaller than the lumen of the delivery tube 20. Once the valve 22 is positioned fully within the delivery tube 20, as seen in FIG. 12, the filaments 130 and adapter 132 are removed.

FIGS. 13-17 illustrate a minimally invasive holder for use with the prosthetic heart valves of the present invention. FIGS. 13A and 13B show the holder 150 attach to the heart valve 22 as described above. The holder 150 includes a multi-armed flexible portion 152 and a rigid portion 154 (seen in FIGS. 17A-17B). The flexible portion 152 includes a plurality, at least three, but preferably six flexible members or arms 156 extending outward from a central circular disk 158. Each of the arms 156 terminates in a rounded end having an attachment aperture 160. The arms 156 are distributed evenly about the circumference of the circular disk 158, and are arrayed to attach to each of the commissures 32 and cusp positioners 42 of the valve 22. Releasable sutures 162 or other such attachment structure are used for this purpose.

Figure 14:
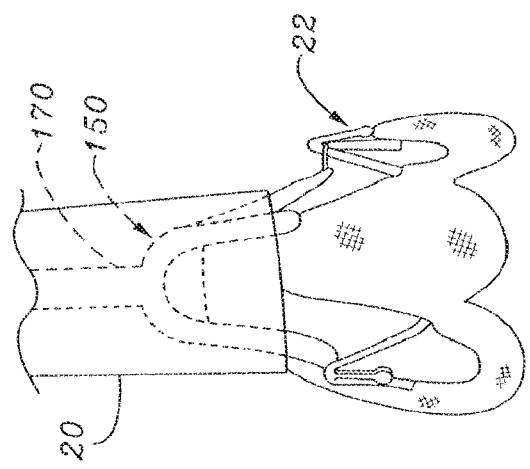
FIG. 14 is a perspective view of the expulsion of an assembled prosthetic heart valve and holder as in FIGS. 13A and 13B from the distal end of a delivery catheter.
Figure 13B:
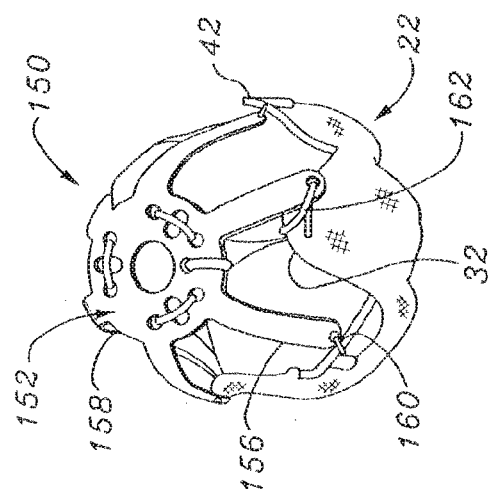

FIG. 14 shows the assembled holder 150 and valve 22 emerging from the distal end of a delivery tube 20. Prior to this stage, the flexible members or arms 156 are oriented generally axially within the tube 20 with the valve 22 also collapsed and having its outflow prongs coupled to the distal ends of the arms 156. The arms 156 of the holder 150 are sufficiently flexible to be compressed into the small profile required for delivery through the delivery tube 20. In this regard, the flexible portion 152 is desirably made of Nitinol. A handle 170 which may be flexible or rigid attaches to the holder 150 for manipulation thereof. Displacing the handle 170 in a distal direction with respect to the tube 20 therefore expels the valve/holder combination and the resiliency of the valve 22 and holder arms 156 causes them to spring outward. It should be understood that other designs of the holder 150 may be utilized, such as replacing the spring-like arms 156 with rigid members that are hinged and spring-biased.

FIGS. 15-17 illustrate specifics of the exemplary flexible portion 152 and rigid portion 154. In a relaxed configuration, the flexible portion 152 is planar, and may be cut from a sheet of Nitinol. The rigid portion 154 includes a proximal face 180 that is sized approximately the same as the circular disk 158, and small enough to fit within the delivery tube 20. A central threaded bore 182 opens to the proximal face 180 for receiving the handle 170. FIG. 15 illustrates a number of sutures 162 threaded through the holder 150 and used to couple the holder to the six outflow prongs of the prosthetic heart valve 22. Desirably, these sutures 162 are anchored with respect to the holder and each one passes over a cutting guide in the holder such that the suture may be severed along its midpoint resulting in two free ends that can be pulled free of the valve.

The holder 150 is sufficiently flexible to be compressed into a small profile and passed through the delivery tube 20. At the same time, the flexible portion 152 and multiple flexible arms 156 have a sufficient degree of torsional strength to permit the operator to rotate the valve 22 during the implant procedure. Furthermore, the arms 156 are shaped to contact the distal mouth of the delivery tube 20 when the assembly is pulled toward the tube which, due to their radial stiffness, causes the arms to bend back toward their axial orientation within the tube. Since the distal ends of the arms are coupled to at least three of the outflow prongs of the prosthetic heart valve 22, the valve constricts accordingly. Constriction of the valve 22 after having been fully expelled from the end of the delivery tube and expanded permits repositioning of the valve 22. That is, the cusp positioners 42 are designed to contact the sinuses cavities or aortic wall after the valve 22 expands, and the retraction/constriction option afforded by the holder 150 may be necessary to disengage the cusp positioners from the surrounding tissue to reposition or re-orient the valve. Furthermore, the valve 22 can be completely collapsed and retracted back into the delivery tube to permit removal in case the surgeon or cardiologist deems the valve unsuitable for whatever reason.

Method of Use

Prior to implant, the cardiac surgeon or cardiologist measures the aortic valve AV annulus using appropriate sizers, minimally invasive or not as the case may be, a number of which are available and which will not be further described herein. The correctly sized valve is then selected and compressed into the delivery catheter or tube 20, such as with the use of the loading adapter 132 having the inner funnel-shaped opening 134 as seen in FIG. 11. To facilitate this loading step, the inner support frame 50 of the valve 20 must be able to withstand high stresses without failure. One method is to form the support frame 50 from a material that has superelastic properties, for instance a Nitinol that has a martensitic transition temperature of less than about 5° C. can be immersed in an ice bath to change its crystalline structure to martensite, which is a superelastic phase. Once loaded into the delivery tube 20, the support frame 50 will not revert back to its original shape upon a temperature rise and thus does not exert undue outward force on the tube. The heart valve 22 may be loaded around an inflation balloon, but for the sake of a small profile the balloon is used after expulsion of the valve from the tube at the implantation site.

With reference again to FIG. 1, the delivery tube 20 is seen in position just prior to complete expulsion and expansion of the prosthetic heart valve 22 from a distal end thereof for implant at the aortic valve AV annulus. The distal end of the delivery tube 20 may optionally be stabilized by a balloon 24 (shown in phantom) inflated against the lumen of the ascending aorta AA, or through other means. The delivery tube 20 is preferably inserted in the vasculature of the patient using a larger diameter introducer 26 through a peripheral vessel such as the femoral artery or femoral vein. Alternatively, the peripheral vessel may be the internal jugular vein, the subclavian artery, the axillary artery, the abdominal aorta, the descending aorta, or any other suitable blood vessel. The introducer 26 may be inserted by surgical cut down or percutaneously using the Seldinger technique.

The prosthetic heart valve 22 is expelled from the delivery tube 20 by relative movement therebetween—i.e., by pushing the valve from the tube or by retracting the tube from around the valve. The valve 22 desirably self-expands into contact with the surrounding lumen wall, but may also be assisted with an inflation balloon or other such physical expander.

With reference to FIGS. 2A and 2B, the cusps positioners 42 help guide the prosthetic heart valve 22 into position in the aortic valve AV annulus. As mentioned above, the cusp positioners 42 desirably flare outward from the rest of the valve structure and are thus configured to contact the sinuses of the aortic valve AV while the cusps 30 are sized to fit within the annulus. In accordance with one method of implantation, the surgeon or cardiologist expels the heart valve 22 below (i.e., toward the left ventricle) its optimum implant position, and then axially displaces the valve upward into the desired position. Stated another way, the heart valve 22 is expanded in a location that is inferior to a final implant position such that the cusp positioners 42 contact the surrounding aortic annulus, and the valve is then repositioned by displacing the valve in a superior direction to a final implant position. As the valve 22 ascends, the cusp positioners 42 spring outward into the three valve sinuses and help rotationally orient the valve. That is, the sinuses channel the cusp positioners 42 and correct any rotational misalignment. Finally, the valve 22 is implanted with the cusp positioners 42 in the sinus cavities (preferably below the coronary ostia CO) and the cusps 30 and cusp connectors 40 forming a scalloped yet continuous contact wall against the aortic valve AV annulus or root.

As mentioned, a physical expander (e.g., balloon) may be used to radially outwardly expand the valve 22 (including the internal support frame 50) beyond its self-expanded diameter so that it is firmly anchored in place. A prosthetic valve possessing hysteresis that is held in a reduced (first or constrained) diameter will exert an outward radial force that is less than the force at which it will resist an inward radial force. Therefore, if deployed in-situ, the device is not expected to exert enough force on the vessel wall to expand to the desired diameter. However, if the expansion is assisted by means of a balloon or other physical expander, the hysteresis of the material will allow it to better maintain its diameter once that diameter is achieved. This is unlike a self-expanding device that relies solely on the outward radial force of the device to achieve its desired diameter. It is also unlike balloon expanded devices that rely on a balloon to plastically deform the device into the desired diameter. Although it is conceivable that a balloon or other physical expander could be used in a self-expanding device made of a material that does not display a hysteresis, the benefits would not be as great.

It will be appreciated that the invention has been described hereabove with reference to certain examples or preferred embodiments as shown in the drawings. Various additions, deletions, changes and alterations may be made to the above-described embodiments and examples, and it is intended that all such additions, deletions, changes and alterations be included within the scope of the following claims.

What is claimed is:

1. A method of positioning a prosthetic heart valve, comprising:

coupling a proximal end portion of a prosthetic heart valve to a distal end portion of an attachment mechanism of a delivery apparatus, wherein a distal end portion of the prosthetic heart valve extends distally beyond the attachment mechanism, the delivery apparatus includes a plurality of deflectable arms, and a plurality of releasable attachment structures extending through the deflectable arms and the prosthetic heart valve;

delivering the prosthetic heart valve through a patient's vasculature to or adjacent the patient's native aortic valve with the prosthetic heart valve retained in a first compressed configuration within a delivery tube of the delivery apparatus;

deploying the prosthetic heart valve from the delivery tube of the delivery apparatus;
allowing radial expansion of the prosthetic heart valve from the first compressed configuration to an expanded configuration at a first position in the patient's body such that the prosthetic heart valve contacts the patient's aortic valve; and
radially constricting the prosthetic heart valve from the expanded configuration to a second compressed configuration greater than the first compressed configuration to disengage the prosthetic heart valve from the patient's aortic valve.

2. The method of claim 1, further comprising repositioning the prosthetic heart valve while in the second compressed configuration from the first position in the patient's body to a second position in the patient's body by axially moving the delivery apparatus relative to the patient's body.

3. The method of claim 2, wherein the first position is inferior to the second position, and repositioning the prosthetic heart valve includes axially moving the delivery apparatus in a superior direction.

4. The method of claim 2, further comprising radially re-expanding the prosthetic heart valve to the expanded configuration after repositioning the prosthetic heart valve to the second position.

5. The method of claim 4, further comprising releasing the prosthetic heart valve from the delivery apparatus after re-expanding the prosthetic heart valve to the expanded configuration.

6. The method of claim 1, further comprising moving the delivery tube back over the prosthetic heart valve to cause the prosthetic heart valve to radially constrict from the second compressed configuration to the first compressed configuration.

7. The method of claim 1, further comprising positioning a plurality of cusp positioners of the prosthetic heart valve in the sinus cavities of the aortic valve.

8. The method of claim 7, wherein the act of positioning the cusp positioners results in the cusp positioners being located below the coronary artery in the sinus cavities.

9. The method of claim 1, at least some of the deflectable arms have distal ends positioned inside of a support frame of the prosthetic heart valve.

10. The method of claim 1, wherein the deflectable arms comprise nitinol.

11. The method of claim 1, wherein a support frame of the prosthetic heart valve comprises three commissures, the delivery apparatus comprises three deflectable arms, and the deflectable arms are circumferentially aligned with and releasably coupled to respective ones of the commissures.

12. The method of claim 11, wherein the delivery apparatus comprises more than three deflectable arms, with some of the deflectable arms releasably coupled to the proximal end portion of the prosthetic heart valve at locations between the commissures.

13. The method of claim 1, wherein a support frame of the prosthetic heart valve comprises three commissures, and wherein each deflectable arm of the delivery apparatus comprises an attachment aperture, and each attachment structure extends through a respective attachment aperture and commissure.

14. The method of claim 13, wherein the attachment structures comprise sutures.

15. A method of positioning a prosthetic heart valve, comprising:
coupling a proximal end portion of a prosthetic heart valve to a distal end portion of a holder of a delivery apparatus, wherein the holder comprises a plurality of radially deflectable arms with apertures formed therein and that are circumferentially aligned with and coupled to respective commissures of a support frame of the prosthetic heart valve, and wherein releasable attachment structures extend through the commissures of the support frame and apertures in the deflectable arms;
delivering the prosthetic heart valve through a patient's vasculature to or adjacent the patient's native aortic valve with the prosthetic heart valve retained in a fully radially compressed configuration within a delivery tube of the delivery apparatus;
deploying the prosthetic heart valve from the delivery tube of the delivery apparatus;
allowing radial expansion of the prosthetic heart valve from the fully compressed configuration to an expanded configuration such that the prosthetic heart valve contacts the patient's aortic valve; and
radially constricting the prosthetic heart valve from the expanded configuration to a partially compressed configuration greater than the fully compressed configuration.

16. The method of claim 15, further comprising:
retrieving the deployed prosthetic heart valve back into the delivery tube of the delivery apparatus; and
removing the prosthetic heart valve from the patient's vasculature.

17. The method of claim 15, further comprising repositioning the prosthetic heart valve relative to the patient's native aortic valve while the prosthetic heart is in the partially compressed configuration.

18. The method of claim 15, wherein radially constricting the prosthetic heart valve to the partially compressed configuration disengages the prosthetic heart valve from the patient's aortic valve.

19. The method of claim 15, further comprising radially re-expanding the prosthetic heart valve to the expanded configuration after repositioning the prosthetic heart valve, and then releasing the prosthetic heart valve from the deflectable arms.

20. The method of claim 19, wherein releasing the prosthetic heart valve from the deflectable arms comprises removing the releasable attachment structures from the commissures and the deflectable arms, which allows the deflectable arms to be de-coupled from the support frame.

21. The method of claim 15, further comprising positioning a plurality of cusp positioners of the prosthetic heart valve in the sinus cavities of the aortic valve.

22. The method of claim 21, wherein the act of positioning the cusp positioners results in the cusp positioners being located below the coronary artery in the sinus cavities.

23. The method of claim 1, wherein the deflectable arms comprise a sufficient degree of torsional strength to permit an operator to rotate the prosthetic heart valve when the prosthetic heart valve is in the expanded configuration.

24. The method of claim 1, wherein the delivery apparatus comprises a shaft, and the deflectable arms extend from a distal end of the shaft and retain a proximal end portion of the prosthetic heart valve axially-spaced from the distal end of the shaft during the acts of delivering and deploying the prosthetic heart valve.

25. A method of positioning a prosthetic heart valve in a native aortic annulus, comprising:
coupling a proximal end portion of a prosthetic heart valve to a plurality of radially deflectable arms that are disposed at a distal end portion of a delivery apparatus;

delivering the prosthetic heart valve through a patient's vasculature to or adjacent the patient's native aortic valve with the prosthetic heart valve and the deflectable arms retained in a fully radially compressed configuration within a delivery tube of the delivery apparatus;

deploying the prosthetic heart valve and the deflectable arms from the delivery tube of the delivery apparatus; and allowing radial expansion of the prosthetic heart valve and the deflectable arms from the fully compressed configuration to an expanded configuration, wherein the deflectable arms are configured to spring radially outwardly to facilitate the radial expansion of the prosthetic heart valve;

wherein the delivery apparatus comprises a shaft and a holder, and wherein the holder comprises the deflectable arms, extends from a distal end of the shaft, and retains a proximal end portion of the prosthetic heart valve axially-spaced from the distal end of the shaft during the acts of delivering and deploying the prosthetic heart valve.

26. A method of positioning a prosthetic heart valve in a native aortic annulus, comprising:

coupling a proximal end portion of a prosthetic heart valve to a distal end portion of a delivery apparatus, wherein the prosthetic heart valve includes a frame comprising nitinol, wherein the distal end portion of the delivery apparatus includes a plurality of radially deflectable arms comprising nitinol, and wherein the prosthetic heart valve and the deflectable arms are biased to an expanded configuration and are compressible to one or more compressed configurations;

radially compressing the prosthetic heart valve and the deflectable arms from the expanded configuration to a fully radially compressed configuration;

delivering the prosthetic heart valve through a patient's vasculature to or adjacent the patient's native aortic valve with the prosthetic heart valve and the deflectable arms retained in the fully radially compressed configuration within a delivery tube of the delivery apparatus;

deploying the prosthetic heart valve from the delivery tube of the delivery apparatus; and allowing radial expansion of the prosthetic heart valve and the deflectable arms from the fully compressed configuration to an expanded configuration.

27. The method of claim 26, wherein the prosthetic heart valve comprises a plurality of leaflets, a support frame having a plurality of commissures, and a plurality of attachment flanges, and wherein pairs of the attachment flanges are coupled to the support frame adjacent the commissures, and each of the leaflets wraps around and is coupled to a respective attachment flange.

28. The method of claim 27, wherein the act of delivering the prosthetic heart valve comprises advancing the distal end portion of the delivery apparatus through an introducer that is inserted into the patient's femoral artery.

* * * * *